US008802132B2

(12) United States Patent
Charest et al.

(10) Patent No.: US 8,802,132 B2
(45) Date of Patent: Aug. 12, 2014

(54) ANTI-MICROBIAL TISSUE PAPER AND PROCESS TO MANUFACTURE SAME

(75) Inventors: Marie-Hélène Charest, Kingsey Falls (CA); Jean-Francois Samuel, Verdun (CA); Pascal Allard, Kingsey Falls (CA); Régis Arsenault, Lachute (CA); Charles Beaulne, Grenville (CA); Jean-Marc Bouchard, Pointe-aux-Trembles (CA); Benoît Graton, Mirabel (CA); Gabriel Sanapo, Victoriaville (CA)

(73) Assignee: Cascades Canada ULC, Montreal, Quebec (CA)

( * ) Notice: Subject to any disclaimer, the term of this patent is extended or adjusted under 35 U.S.C. 154(b) by 24 days.

(21) Appl. No.: 13/522,735

(22) PCT Filed: Jan. 18, 2011

(86) PCT No.: PCT/CA2011/050021
§ 371 (c)(1),
(2), (4) Date: Jul. 18, 2012

(87) PCT Pub. No.: WO2011/085499
PCT Pub. Date: Jul. 21, 2011

(65) Prior Publication Data
US 2012/0301536 A1 Nov. 29, 2012

Related U.S. Application Data

(60) Provisional application No. 61/295,990, filed on Jan. 18, 2010.

(51) Int. Cl.
| A61K 9/70 | (2006.01) |
| A61F 13/00 | (2006.01) |
| D21H 21/36 | (2006.01) |
| A61L 15/28 | (2006.01) |
| A61L 15/44 | (2006.01) |
| A61L 15/46 | (2006.01) |
| A01N 33/12 | (2006.01) |
| A01N 25/34 | (2006.01) |
| D21H 17/44 | (2006.01) |
| D21H 21/24 | (2006.01) |
| D21H 27/00 | (2006.01) |

(52) U.S. Cl.
CPC ............. *A01N 25/34* (2013.01); *A61L 233/406* (2013.01); *A61L 2300/802* (2013.01); *D21H 17/44* (2013.01); *A61L 2300/208* (2013.01); *D21H 21/36* (2013.01); *A61L 2300/408* (2013.01); *A61L 15/28* (2013.01); *A61L 2300/404* (2013.01); *A61L 15/44* (2013.01); *A61L 15/46* (2013.01); *A61L 2300/204* (2013.01); *A01N 33/12* (2013.01); *D21H 21/24* (2013.01); *D21H 27/002* (2013.01)
USPC .......................................................... 424/442

(58) Field of Classification Search
None
See application file for complete search history.

(56) References Cited

U.S. PATENT DOCUMENTS

| 2,756,647 | A | | 7/1956 | Thompson |
| 3,138,533 | A | | 6/1964 | Heim et al. |
| 3,227,614 | A | | 1/1966 | Scheuer |
| 3,728,213 | A | * | 4/1973 | Hinz .............................. 162/161 |
| 4,122,158 | A | | 10/1978 | Schmitt |
| 4,351,699 | A | | 9/1982 | Osborn, III |
| 4,441,962 | A | | 4/1984 | Osborn, III |
| 4,533,435 | A | | 8/1985 | Intili |
| 5,152,996 | A | | 10/1992 | Corey et al. |
| 5,156,843 | A | | 10/1992 | Leong et al. |
| 5,707,736 | A | | 1/1998 | Levy et al. |
| 6,245,197 | B1 | | 6/2001 | Oriaran et al. |
| 6,270,878 | B1 | | 8/2001 | Wegele et al. |
| 6,325,969 | B1 | | 12/2001 | Aamodt et al. |
| 6,338,855 | B1 | | 1/2002 | Albacarys et al. |
| 6,547,928 | B2 | | 4/2003 | Barnholtz et al. |
| 6,712,121 | B2 | | 3/2004 | Clark et al. |
| 6,916,480 | B2 | | 7/2005 | Anderson et al. |
| 7,285,283 | B2 | | 10/2007 | Baumoeller et al. |
| 7,622,021 | B1 | | 11/2009 | Baumoeller et al. |
| 7,887,673 | B2 | * | 2/2011 | Andersson et al. ........... 162/202 |
| 2003/0157856 | A1 | | 8/2003 | Schroeder et al. |

| | | | |
|---|---|---|---|
| 2004/0161450 | A1 | 8/2004 | Buder |
| 2005/0133176 | A1 | 6/2005 | Vinson et al. |
| 2006/0021150 | A1 | 2/2006 | Hu et al. |
| 2007/0237807 | A1 | 10/2007 | Luu et al. |
| 2007/0295465 | A1 | 12/2007 | Dyer et al. |
| 2008/0000602 | A1 | 1/2008 | Dyer et al. |
| 2009/0104430 | A1 * | 4/2009 | Cordial et al. ............. 428/322.7 |

FOREIGN PATENT DOCUMENTS

| | | |
|---|---|---|
| CA | 2630112 | 8/2007 |
| CA | 2653597 | 1/2008 |
| CO | 5680106 | 9/2006 |
| DE | 102005021364 | 11/2006 |
| GB | 2109237 A | 6/1983 |
| WO | 2007024972 | 3/2007 |
| WO | 2007024974 | 3/2007 |
| WO | 2008002420 | 1/2008 |

OTHER PUBLICATIONS

Tarik Jabrane; et al., Bacteriophage Immobilization on Paper Surface: Effect of Cationic Pre-coat Layer, Proceeding of PAPTAC 95th Annual Meeting, 2009 and pp. 311 to 315.

Tarik Jabrane; et al., Bacteriophage Activity on Paper Surface: Effect of Paper Moisture, Proceedings of 8th World Congress of Chemical Engineering, 2009 and pp. 1 to 6.

* cited by examiner

*Primary Examiner* — Anand Desai
*Assistant Examiner* — Melissa Mercier
(74) *Attorney, Agent, or Firm* — Sutherland Asbill & Brennan LLP

(57) ABSTRACT

An antimicrobial paper includes a paper web having a grammage between 10 and 60 grams per square meter, a cationizing agent in a concentration ranging between 0.05 wt % and 5 wt %, an antimicrobial agent in a concentration ranging between 0.01 wt % and 3 wt %, the antimicrobial agent and the cationizing agent being added on the paper web having a consistency above 15 wt %, the antimicrobial paper having an antimicrobial agent release of above about 0.01 wt % when wetted.

33 Claims, 11 Drawing Sheets

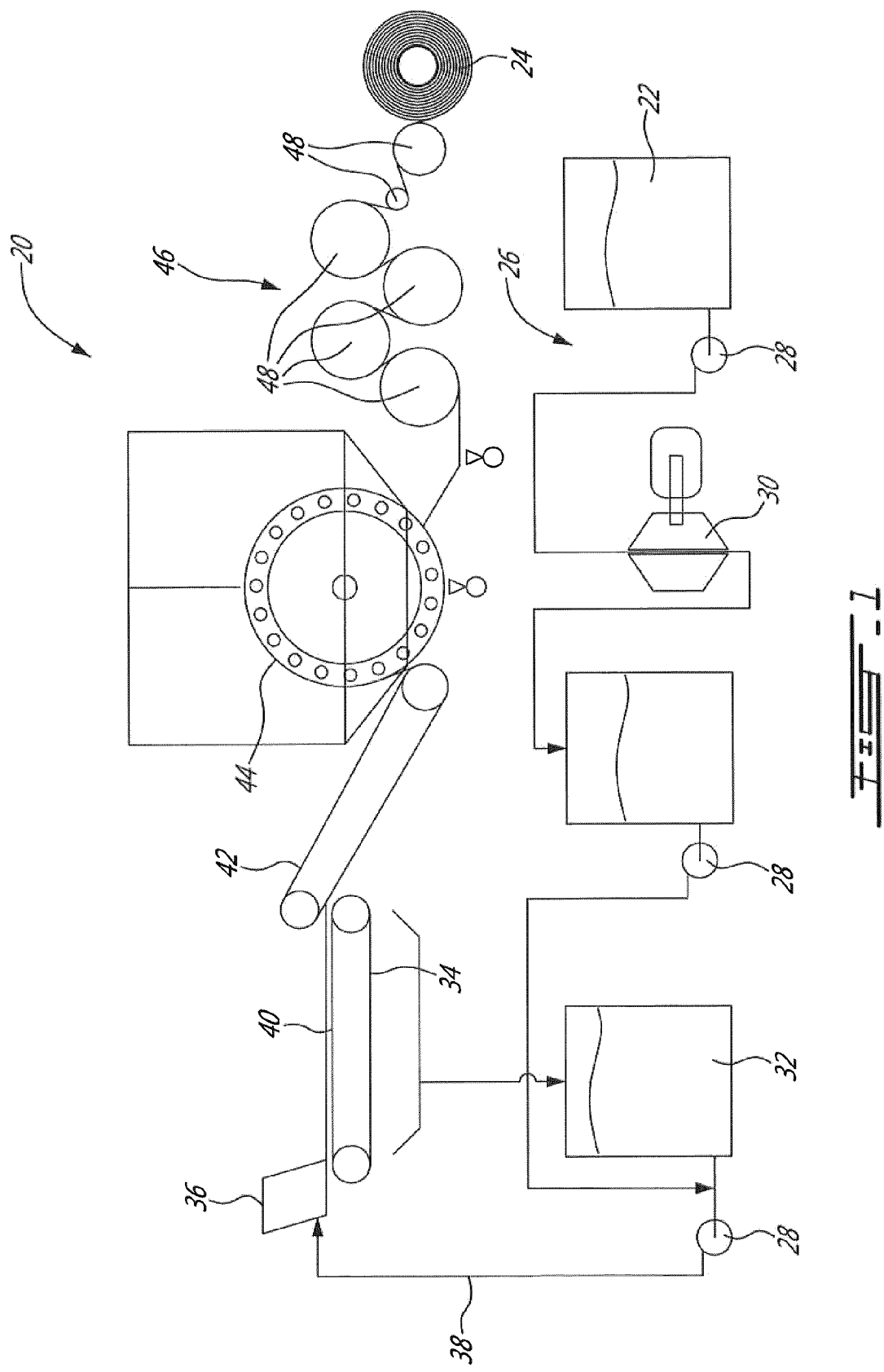

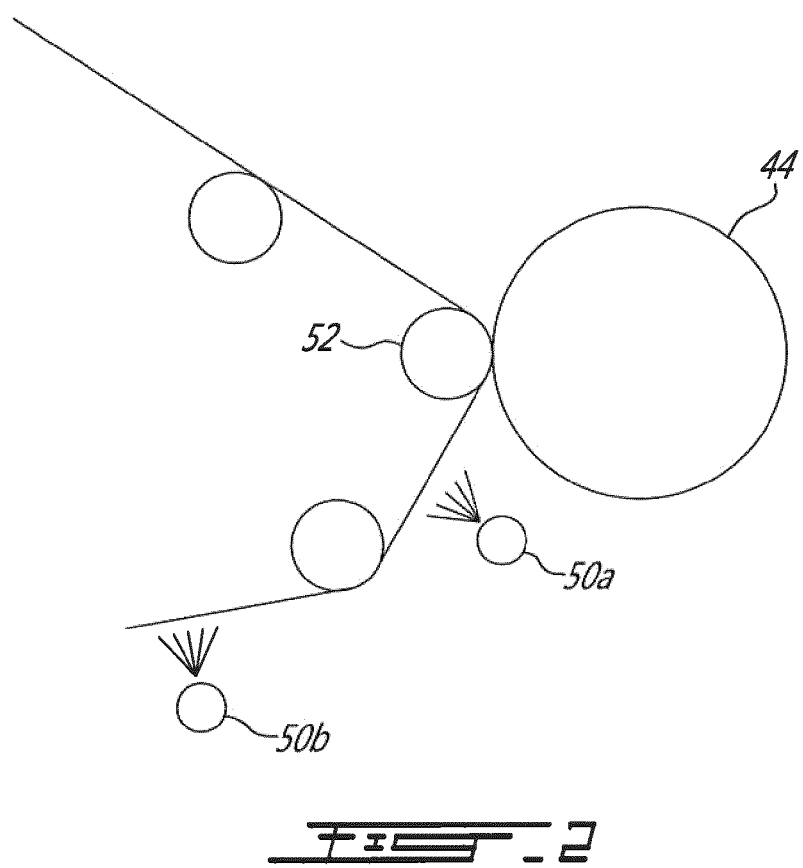
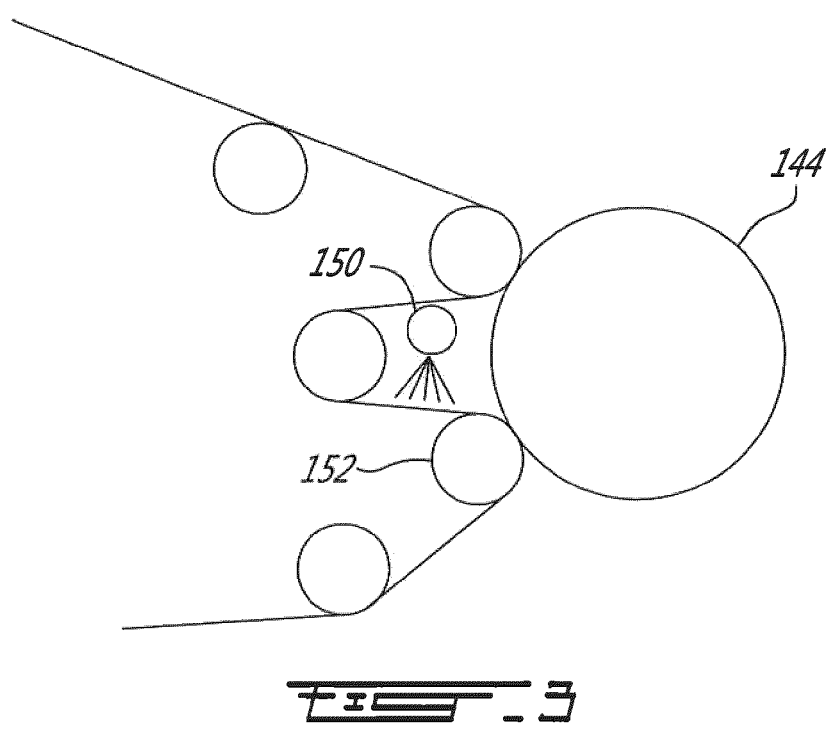

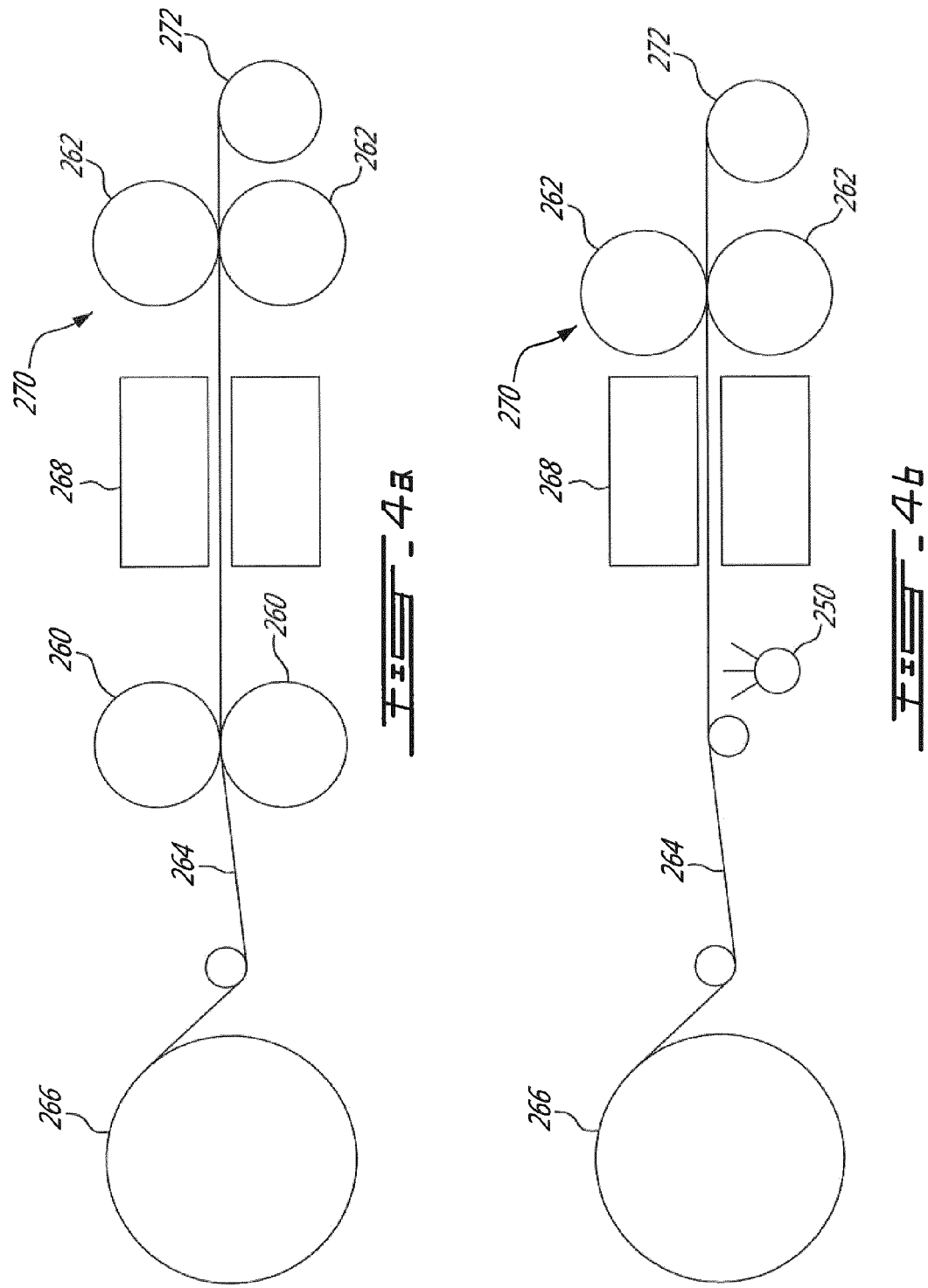

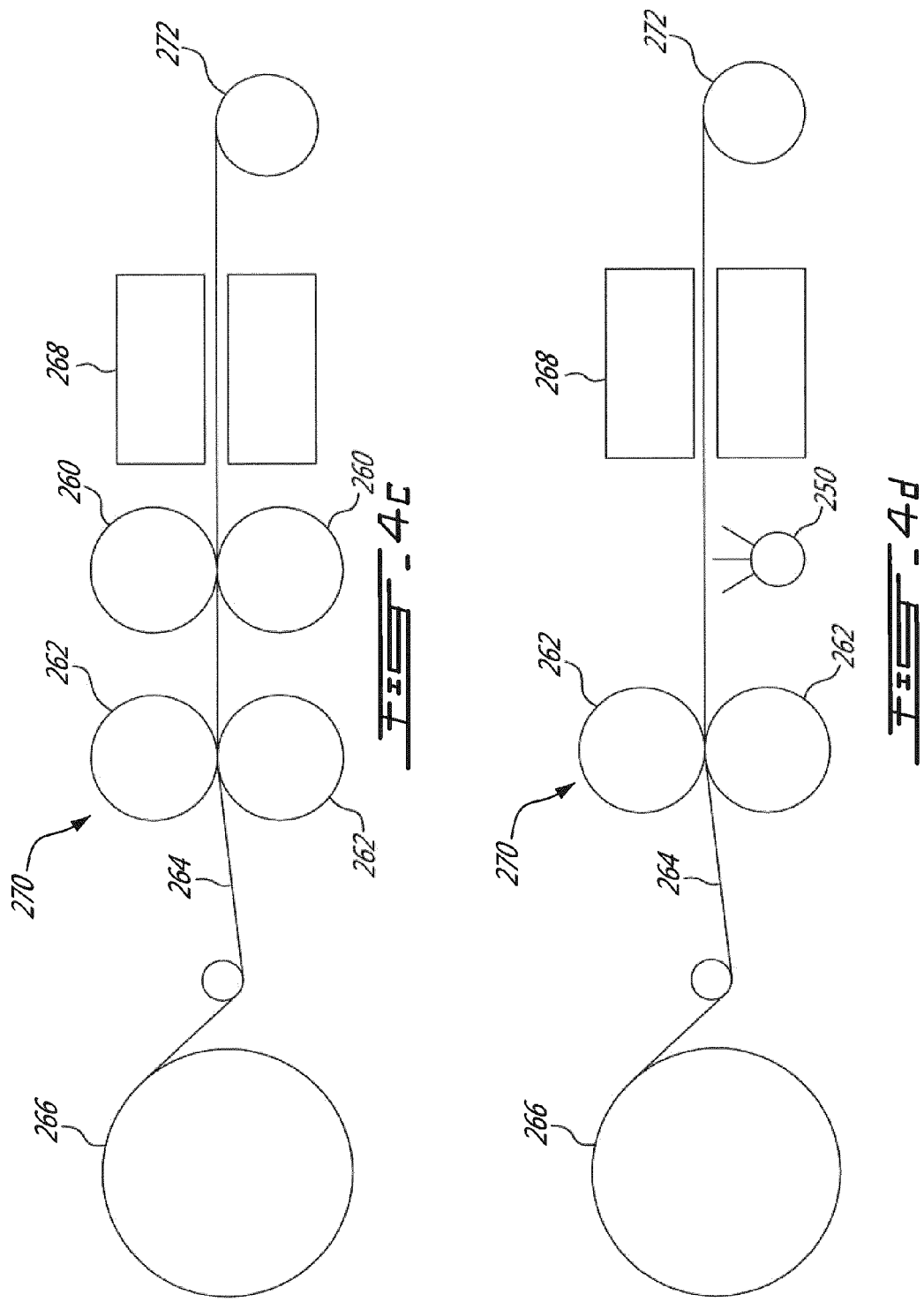

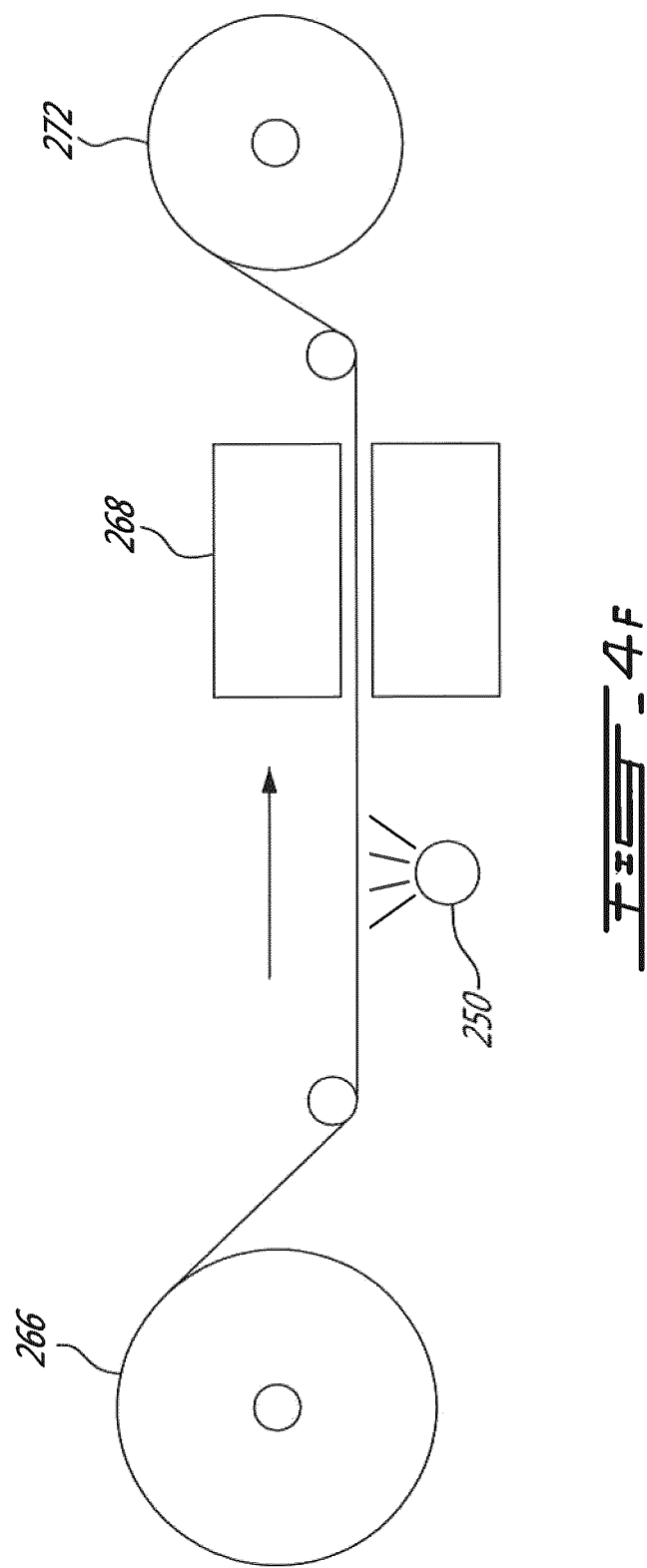

ANTI-MICROBIAL TISSUE PAPER AND PROCESS TO MANUFACTURE SAME

CROSS-REFERENCE TO RELATED APPLICATIONS

This application claims priority under 35 USC §119(e) of U.S. provisional patent application 61/295,990 filed on Jan. 18, 2010, the specification of which is hereby incorporated by reference. This application is a national phase entry of PCT patent application serial number PCT/CA2011/050021 filed on Jan. 18, 2011, designating the United States of America.

TECHNICAL FIELD OF THE INVENTION

The technical field relates to an antimicrobial tissue paper and, more particularly, to an antimicrobial tissue paper including an antimicrobial agent and a cationizing agent and to a process to manufacture same.

BACKGROUND

Antimicrobial papers are generally obtained by producing the paper in a sheet form and coating the sheet with an antimicrobial coating to inhibit, reduce or kill microorganisms (for instance and without being limitative, fungi, viruses, and bacteria) thereon. However, these coatings are easily rubbed off or otherwise destroyed by unsuitable storage or shipping. Once the coating has been destroyed, there is no further antimicrobial action to protect the paper or to inhibit microorganism growth.

Furthermore, the antimicrobial agent remains attached/adsorbed to the paper sheet and is not released on the surface or body part when contacted therewith. Even when wetted, there is no antimicrobial agent release. Therefore, the surface or body part which has been in contact with the antimicrobial paper is not protected by the antimicrobial agent when the paper is removed therefrom.

BRIEF SUMMARY OF THE INVENTION

It is therefore an aim of the present invention to address the above mentioned issues.

According to a general aspect, there is provided an antimicrobial paper comprising a paper web having a grammage between 10 and 60 grams per square meter, a cationizing agent in a concentration ranging between 0.05 wt % and 5 wt %, an antimicrobial agent in a concentration ranging between 0.01 wt % and 3 wt %, the antimicrobial agent and the cationizing agent being added on the paper web having a consistency above 15 wt %.

According to a general aspect, there is provided a process for manufacturing an antimicrobial paper having a consistency above 92 wt %, comprising: obtaining a paper web having a solid content above 15 wt %; and applying a cationizing agent in a concentration ranging between 0.05 wt % and 5 wt % and an antimicrobial agent in a concentration ranging between 0.01 wt % and 3 wt %; drying the paper web to increase the consistency above 92 wt %.

In an embodiment, the antimicrobial agent is water soluble and a portion of the antimicrobial agent is released when the antimicrobial paper is wetted. The antimicrobial paper can have an antimicrobial agent release of above about 0.01 wt % when wetted in an embodiment, and above about 0.05 wt % when wetted in an alternative embodiment. In still another embodiment, the antimicrobial agent release is between 0.05 wt % and 0.6 wt % when wetted.

In an embodiment, the antimicrobial agent is a surfactant, which can be cationic. The antimicrobial agent can be an amine salt and, more particularly, a quaternary ammonium. The antimicrobial agent can have antimicrobial properties against at least one type of bacteria, at least one type of fungi, or at least one virus.

In an embodiment, the cationizing agent is added in a concentration sufficient to partially neutralize or cationize the paper web. The cationizing agent can be in a concentration below 2.5 wt %. The cationizing agent can have a charge density above about 2 eq/kg, in an alternative embodiment, above about 5 eq/kg, and, in another alternative embodiment, above about 7 eq/kg. The cationizing agent can have a molecular weight below 1000 kDa and, in an alternative embodiment below about 500 kDa. In an embodiment, the cationizing agent is an organic coagulant. In an embodiment, the cationizing agent is at least one of a polyamine, a polydiallyldimethylammonium chloride (polyDADMAC), a polyethyleneimine (PEI), a polyamine-epichlorohydrin (PAE), a polyamidoamine-epichlorohydrin (PAAE), and a polyvinylamine (PVAm).

In an embodiment, the paper web has a thickness ranging between 125 and 1000 micrometers. In an embodiment, the paper web comprises one to five superposed paper plies. In an embodiment, the paper web is a tissue paper. The tissue paper can be embossed.

In an embodiment, the cationizing agent and the antimicrobial agent are added to the paper web in a paper machine following a Yankee dryer and before at least one afterdryer. In an embodiment, the cationizing agent and the antimicrobial agent are applied by a spraying system.

In an embodiment, the cationizing agent and the antimicrobial agent are added to the paper web having a consistency between 80 wt % and 92 wt %.

According to another general aspect, there is provided a process for manufacturing an antimicrobial paper having a consistency above 92 wt %, comprising: obtaining a paper web having a consistency above 15 wt %; applying a cationizing agent in a concentration ranging between 0.05 wt % and 5 wt % and an antimicrobial agent in a concentration ranging between 0.01 wt % and 3 wt % to the paper web having a consistency above 15 wt %; and drying the paper web including the cationizing agent and the antimicrobial agent to increase the consistency above 92 wt %. A portion of the antimicrobial agent is released when the antimicrobial paper is wetted.

In an embodiment, the paper web is dried following the application of the cationizing agent and the antimicrobial agent.

In an embodiment, the paper web has a grammage between 10 and 60 grams per square meter.

In an embodiment, the application further comprises spraying the cationizing agent and the antimicrobial agent to the paper web.

According to another general aspect, there is provided an antimicrobial paper comprising a paper web including a cationizing agent in a concentration ranging between 0.05 wt % and 5 wt %, a water soluble antimicrobial agent in a concentration ranging between 0.01 wt % and 3 wt % and having an antimicrobial agent release rate of above about 0.01 wt % when wetted.

In an embodiment, the antimicrobial agent and the cationizing agent being added on the paper web having a consistency above 15 wt %.

In this specification, the term "antimicrobial" is intended to mean that there is a bactericidal and/or a bacteriostatic and/or fungicidal and/or fungistatic effect and/or a virucidal effect wherein the term "bactericidal" is to be understood as capable of killing bacterial cells, the term "bacteriostatic" is to be understood as capable of inhibiting bacterial growth, i.e. inhibiting growing bacterial cells, the term "fungicidal" is to be understood as capable of killing fungal cells, the term "fungicistatic" is to be understood as inhibiting fungal growth, the term "virucidal" is to be understood as capable of inactivating virus.

In the context of the present invention the term "inhibiting growth of microbial cells" is intended to mean that the cells are in the non-reproductive state.

In this specification, the term "cationizing agent" is intended to mean any agent which has positive charges that interacts with the paper anionic charges to at least partially neutralize the anionic charge. The cationizing agent can include a cationic polymer.

BRIEF DESCRIPTION OF THE DRAWINGS

FIG. 1 is a schematic flowchart of a process for manufacturing an antimicrobial tissue paper in accordance with a first embodiment;

FIG. 2 is a schematic flowchart of a section of the process for manufacturing the antimicrobial tissue paper showing a first embodiment for adding a cationizing agent and an antimicrobial agent before a Yankee dryer;

FIG. 3 is a schematic flowchart of a section of the process for manufacturing the antimicrobial tissue paper showing a second embodiment for adding the cationizing agent and the antimicrobial agent before the Yankee dryer;

It will be noted that throughout the appended drawings, like features are identified by like reference numerals.

DETAILED DESCRIPTION

Figure 4E:
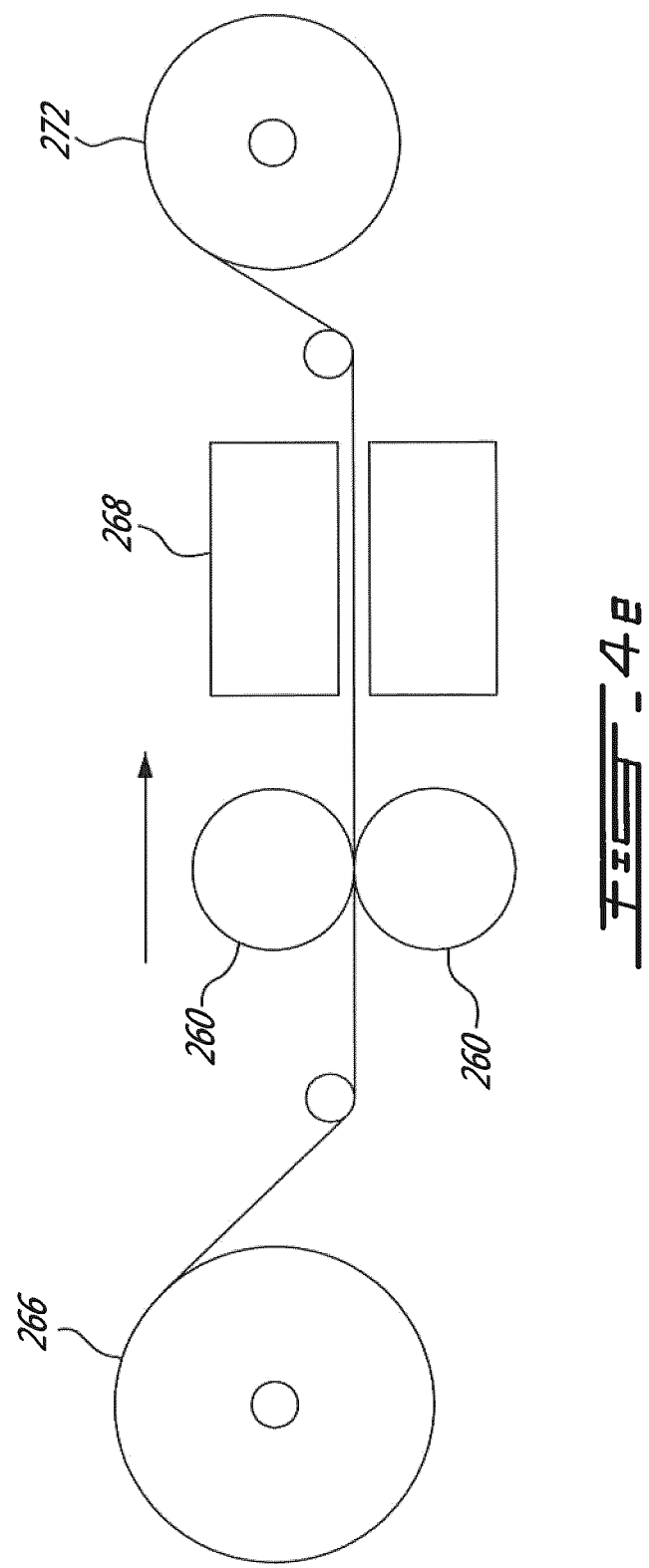
FIG. 4 includes FIGS. 4a, 4b, 4c, 4d, 4e, and 4f and are schematic flowchart of a section of the process for manufacturing the antimicrobial tissue paper showing a third embodiment for adding the cationizing and the antimicrobial agents wherein the cationizing and the antimicrobial agents are added during the paper converting, in FIG. 4a, the agents are added by applicator rolls upstream of the embossing rolls, in FIG. 4b, the agents are added by a spray shower upstream of the embossing rolls, in FIG. 4c, the agents are added by applicator rolls downstream of the embossing rolls, in FIG. 4d, the agents are added by a spray shower downstream the embossing rolls, in FIG. 4e, the agents are added by applicator rolls without embossing rolls, and in FIG. 4f, the agents are added by a spray shower without embossing rolls.

The antimicrobial tissue paper is a bioactive paper which includes an antimicrobial agent and a cationizing agent. The antimicrobial tissue paper releases at least a portion of its antimicrobial agent content when wetted. The released antimicrobial agent kills at least some of the microorganisms including bacteria on a surface including a person's body part or a surface where the antimicrobial agent is released. Furthermore it leaves a residual antimicrobial activity on skin or on a surface, as it will be described in more details below.

The antimicrobial agent release refers to the antimicrobial agent found on a surface after wiping the originally wetted surface with an antimicrobial treated paper. In other words, a portion of the antimicrobial agent content adsorbed on the paper fibres desorbs and/or is released when the paper is wetted.

The tissue paper is a lightweight paper, which can be a creped paper. In an embodiment, the tissue paper has a grammage below approximately 60 grams per square meter (g/m$^2$). In another embodiment, the tissue paper has a grammage ranging between approximately 10 to 60 g/m$^2$ and, in an alternative embodiment, it has a grammage ranging between approximately 20 to 50 g/m$^2$.

In an embodiment, the tissue paper has a thickness ranging between 125 and 1000 micrometers. In another embodiment, the tissue paper has a thickness ranging between 150 and 600 micrometers and, in an alternative embodiment, it has a thickness ranging between approximately 200 and 300 micrometers.

For instance and without being limitative, the tissue paper can be made from cellulosic and/or lignocellulosic fibres which can be virgin fibres from softwood and/or hardwood species, recycled bleached or unbleached paper, or a combination thereof, recycled fibres obtained from recycled paper and paper machine and converting tailings, or combinations thereof. In an embodiment, the cellulosic and/or lignocellulosic fibres include wood fibres. The tissue paper can be unbleached (brown) or bleached. The tissue paper includes one ply to ten superposed plies. In another embodiment, the tissue paper can be one to five plies and, in another alternative embodiment, the tissue paper can be one to three plies.

Table 1 shows examples of the mechanical properties of three antimicrobial tissue papers that can be used as paper substrate for the antimicrobial paper.

TABLE 1

Mechanical properties of three antimicrobial tissue papers.

| | Napkins | | Bathroom tissue | | Facial tissue | | Hand and household towels | |
|---|---|---|---|---|---|---|---|---|
| | Min. gf/po | Max. gf/po | Min. gf/po | Max. gf/po | Min. gf/po | Max. gf/po | Min. gf/po | Max. gf/po |
| MDDT | 400 | 1200 | 150 | 650 | 225 | 700 | 550 | 3000 |
| CDDT | 230 | 570 | 80 | 220 | 70 | 500 | 350 | 2000 |
| MDWT | N/A | N/A | 5 | 200 | 30 | 225 | 120 | 1000 |
| CDWT | N/A | N/A | 5 | 100 | 15 | 150 | 70 | 700 |

MDDT: Machine direction dry tensile;
CDDT: Cross-direction dry tensile;
MDWT: Machine direction wet tensile;
CDWT: Cross-direction wet tensile;
gf/po: grams-force per inch.

The antimicrobial and cationizing agents are added during the manufacturing process of the tissue paper, after the forming section. For instance, they can be applied at the paper machine after the forming section or during the following converting step, if any. In the paper machine, the antimicrobial and the cationizing agents can be applied before or after the Yankee dryer, before the after-dryers, as it will be described in more details below. More particularly, they are added while the paper web has a solid content above about 15 wt % and, in an embodiment, between approximately 90 wt % and 98 wt %, in an alternative embodiment, between approximately 75 wt % and 95 wt %, and, in an alternative embodiment, between approximately 20 wt % and 50 wt %.

If they are applied during the converting step, further drying may be necessary to dry the tissue paper following the addition of the antimicrobial and cationizing agents.

The cationizing and antimicrobial agents can be applied simultaneously or sequentially. If they are applied sequentially, the cationizing agent is applied before the antimicrobial agent to at least partially neutralize the paper anionic charges, as it will be described in more details below. If they are applied simultaneously, they can be applied separately or together as a solution containing both agents using two or more application systems or together in one application system.

The antimicrobial agent is added to the paper web in a concentration ranging between approximately 0.01 wt % to 3 wt %, i.e. between 0.1 and 30 kilograms per ton of paper. In an alternative embodiment, the antimicrobial concentration is below about 1 wt %, i.e. below 10 kilograms per ton of paper, in an alternative embodiment, the antimicrobial concentration is below about 0.5 wt %, i.e. below 5 kilograms per ton of paper, and in still an alternative embodiment, the antimicrobial concentration ranges between about 0.1 wt % and 0.4 wt %, i.e. between 1 and 4 kilograms per ton of paper. In another alternative embodiment, the antimicrobial concentration ranges between about 0.2 wt % and 0.3 wt %, i.e. between 2 and 3 kilograms per ton of paper.

The cationizing agent is added to the paper web in a concentration ranging between approximately 0.05 wt % and 5 wt %, i.e. between 0.5 and 50 kilograms per ton of paper. In an alternative embodiment, the cationizing agent is added to the paper web in a concentration ranging between about 0.1 wt % and 2.5 wt %, i.e. between 1 and 25 kilograms per ton of paper, in an alternative embodiment, the cationizing agent concentration ranges between about 1 wt % and 2 wt %, i.e. between 10 and 20 kilograms per ton of paper, and still in an alternative embodiment, the cationizing agent concentration ranges between about 1.2 wt % and 2.5 wt %, i.e. between 12 and 25 kilograms per ton of paper.

As further described below, the concentration of the cationizing agent varies in accordance with its charge density and its molecular weight as well as the paper anionic charges.

The antimicrobial and cationizing agent concentrations can be selected in accordance with the paper properties. For instance and without being limitative, lower antimicrobial and cationizing agent concentrations may be added to tissue papers having lower intrinsic charge density in comparison with tissue papers having higher intrinsic charge density, as it will be described in more details below.

The antimicrobial agent is soluble in water to be at least partially released when the paper support is wetted. In a particular embodiment, the antimicrobial agent is cationic. The antimicrobial agent can also be a surfactant.

It can be selected from the group of amine salts and, more particularly, quaternary ammoniums (including first and higher generations of quaternary ammonium compounds). In an embodiment, the amine salts and the quaternary ammoniums are cationic. Furthermore, the amine salts and the quaternary ammoniums have antimicrobial properties. For instance and without being limitative, the quaternary ammoniums can include:

benzalkonium chloride (N-Alkyl-N,N-dimethyl-N-benzylammonium chloride or ADBAC), cetyltrimethylammonium bromide (CTAB),
cetyltrimethylammonium chloride (CTAC),
benzenthonium chloride;
di-n-decyl-dimethylammonium chloride (DDAC),
diallyl-dimethylammonium chloride (DMDAC), and
1-hexadecylpyridinium chloride (HDPC).

For instance and without being limitative, the amine salts can be:

poly(hexamethylene biguanide) hydrochloride (PHMB), and
chlorhexidine salts such as 1,6-Di-(4-chlorophenyl-diguanide)-hexan digluconate (chlorhexidine digluconate).

In an embodiment, the antimicrobial agent can include a mixture of several components to broden the antimicrobial spectrum. For instance and without being limitative, it can include a mixture of dioctyl-dimethylammonium chloride, didecyl-dimethylammonium chloride, octyl-decyl-dimethylammonium chloride, and benzalkonium chloride.

The antimicrobial agent can be a bactericide as well as a virucide, a germicide, a fungicide or any combination thereof. One skilled in the art will appreciate that the scope of antimicrobial activity of the resulting antimicrobial paper can vary in accordance with antimicrobial agents used.

In an embodiment, the antimicrobial agent is benzalkonium chloride, a surfactant. Benzalkonium chloride is soluble in water, heat stable, low odor, colorless, has a low toxicity for humans when released, germicide in relatively low concentrations, compatible in pulp and paper processes, stable in various pH and various water hardnesses, and has a good affinity to the paper fibres.

It is appreciated that, as mentioned above, different antimicrobial agents can be used or combinations of several antimicrobial agents can be applied to the paper substrate. The scope of antimicrobial activity varies in accordance with the antimicrobial agents used.

The cationizing agent can be an organic compound which at least partially neutralizes the paper ionic charges and improves the release of a portion of the antimicrobial agent. In other words, the tissue paper has anionic charges (negative charges) and the cationizing agent at least partially neutralizes the paper anionic charges. In an embodiment, the cationizing agent is a cationic polyelectrolyte.

The antimicrobial agent release is related to the degree of neutralization of the paper substrate by the cationizing agent. When the paper is wetted, the degree of neutralization affects the release of the antimicrobial agent that was previously applied on the paper web.

Amongst others, the following parameters associated to the cationizing agent influence the antimicrobial agent release rate: the chemical nature of the cationizing agent, its molecular weight, and its charge density.

The charge density of the cationizing agent is an important parameter to control the release rate of the antimicrobial agent. As it will be described in more details below, a cationizing polymer having a higher charge density will neutralize or cationize an increased portion of cellulosic fibre charges and therefore increase the antimicrobial agent release rate in comparison with the same concentration of a cationizing polymer having a lower charge density.

The molecular weight of the cationizing agent is also an important variable to control the release of the antimicrobial agent. As it will be described in more details below, a cationizing polymer having a low molecular weight (below about 250 kDa) will enhance the antimicrobial agent release in comparison with the same concentration of a cationizing polymer having a medium molecular weight (between about 250 kDa and 1000 kDa) or a high molecular weight (above about 1000 kDa), when both polymers have substantially the same charge density.

Following the addition of the cationizing agent to the paper substrate, the total paper ionic charges can be still anionic, cationic or neutral.

To enhance the neutralization of most anionic charges, the cationizing agent should have a relatively low or medium molecular weight, i.e. about smaller than 250 kDA, to facilitate its penetration within the fibers.

In an embodiment, the cationization agent can be any molecule, including polymers, capable of neutralizing negative fibre charges. For instance, the cationizing agents can be selected from the products listed in Table 2.

TABLE 2

Examples of cationizing agents.

| Product | Acronym | Charge Density (pH = 7) (Equiv/ Kg dry) | Molecular weight (kDa) |
|---|---|---|---|
| Polyamines | Poly-quat, EPI-DMA | 6-9.9 | ~10-500 |
| Polyethyleneimine | PEI | 6-8 | ~100-2000 |
| Polydiallyldimethylammonium chloride | Poly-DADMAC | 8-13 | ~100-2000 |
| Polyamidoamine-epichlorohydrin | PAAE | 2-4 | ~40-200 |
| Polyamine-epichlorohydrin | PAE | 2-4 | ~200 |
| Cationic polyacrylamide (medium molecular weight) | C-PAM | 2-3.5 | ~500-1000 |
| Hydrolyzed or partially hydrolyzed polyvinylformamide (polyvinylamine) | PVAm, PVFA/ PVAm | 1.5-13 | ~50-1200 |
| Cationic starches (for instance, waxy maize, corn, wheat, potato, rice, or tapioca starches) | C-starch | 0.62 | |
| Glyoxalated polyacrylamide | G-PAM | 0.3-0.6 | ~20-100 |
| Cationic polyacrylamide (high molecular weight) | C-PAM | 0.5-2 | ~1000-15 000 |
| Any copolymers from the above mentioned families of polymers | | | |

Other embodiments of cationizing agents can include, without being limitative:
- sulfuric acid,
- phosphoric acid,
- alum (aluminium sulfate), and
- hydrochloric acid.

In an embodiment, the cationizing agent is polyepichlorohydrin-dimethylamine, a cationic agent which is characterized by a substantially low molecular weight polyamine (50 kDa) with a relatively high charge density (between about 6 and 9.9 Equiv/Kg dry. The addition of polyepichlorohydrin-dimethylamine to the tissue paper does not affect the pH or the texture of the tissue paper.

As mentioned above, the cationizing agent at least partially neutralizes the paper anionic charges. Thereby, a portion of the antimicrobial agent, which can also be cationic, is not retained on the tissue paper when the latter is wetted and is thereby released. In an embodiment, the tissue paper has a release rate between approximately 0.01 wt % and 0.6 wt % when wetted. In an alternative embodiment, the tissue paper has a release rate between approximately 0.05 wt % and 0.2 wt % when wetted. For example, a tissue paper containing about 0.3 wt % of antimicrobial agent can release about 0.1 wt % of antimicrobial agent when wetted. The antimicrobial agent released from the tissue paper is measured relatively to the original, substantially dry tissue paper weight including the cationizing and antimicrobial agents. The antimicrobial agent released from the tissue paper is measured in a solution, such as water, following extraction. For the release rates mentioned in the application, the extraction is carried out by the lab blender method described below. The antimicrobial agent in the solution is measured by a method such as and without being limitative biphasic titration or high performance liquid chromatography (HPLC).

As it will be described in more details below, the addition of a cationizing agent in combination with the antimicrobial agent enhances the release of a portion of the antimicrobial agent from a wetted antimicrobial tissue paper. The cationizing agent at least partially neutralizes the paper anionic charges. In the absence of the cationizing agent, some of the antimicrobial agent, which is cationic, will neutralize the paper charges and therefore the amount of antimicrobial agent released will be lower.

Referring to FIG. 1, there is shown a process for manufacturing an antimicrobial tissue paper in accordance with an embodiment.

The tissue paper is produced on a paper machine 20, such as a Fourdrinier machine, which transforms the cellulosic pulp 22 into a final paper-based product 24.

The wet end 26 is the first section of the paper machine 20. Pulp 22 is delivered in a slurry form, i.e. a mixture of fibres, water, and other additives, from a pulping process. Fibres can include recycled paper fibres, virgin fibres, paper machine and converting tailings, and mixture thereof. Water can be fresh water, white water or mixture thereof. Pulp is fed by pumps 28 to refiners 30 where fibres are subjected to high pressure pulses between bars on rotating refiner discs. After refining, the pulp is mixed with some of the following: sizing, fillers, dyes, pigments, optical brightner agents (OBA), retention aid, wet and dry strength agents, and the like. One skilled in the art will appreciate that some additives can be added prior to refining. In an embodiment, a wet strength agent is added to provide wet strength resistance. About 0.02 wt % to about 1 wt % (0.2 to 10 kilograms per ton of pulp) of wet strength agent can be added to the pulp to improve the wet strength resistance.

White water 32, which may be filtered and is contained in a chest, can be added to the paper stock following the refiners 30 to further dilute the paper stock. White water is water that falls through a moving wire mesh conveyor 34 following a head box 36, as it will be described in more details below. It contains fine fibre particles.

Between each step, the pulp or paper stock is contained in tanks or chests (at low, medium or high consistency, depending on the process and equipments) and pumps carry the pulp or paper stock between the process equipments.

The stock 38 then enters the headbox 36, a unit that disperses and homogenizes the paper stock and loads it onto the moving wire mesh conveyor 34. The paper stock is spread substantially uniformly on the moving wire 34 as a wet mat. A gate, also referred to as slice, is used to control the basis weight profil, the consistency of the pulp slurry and thickness of the paper web. The wire revolves around the Fourdrinier table 40. Beneath the Fourdrinier table are suction boxes, which remove the water from the web with the help of vacuum. The solid content of the paper stock varies between about 0.2 wt % to about 20 wt % between the input and the output of the Fourdrinier table 40.

It is appreciated that, in alternative embodiments, the pulp can be spread substantially uniformly on other forming apparatuses such as and without being limitative to a C-former, a twin wire former, a crescent former, a through air-dried (TAD) technology, an uncreped through air dried (UCTAD)

technology, Structured Tissue Technology (STT), Atmos, any equivalent TAD paper (ETAD) products, suction breast roll formers, inclined suction breast roll formers, and the like.

The wet mat is transferred from the forming section to a press section wherein most water remaining in the web is removed via a system of nips formed by rolls pressing against each other, called press(es) such as conventional presses and shoe presses. In addition to helping remove more of the water, the press section smoothes and flattens out the wet mat in the shape of a sheet. Presses can have suction or non-suction rolls to help in the water removal process. The press section generally includes one or two presses. In the embodiment shown a suction press 42 uses mechanical action to extract the water from the wet mat. On a tissue machine, the press is located against the Yankee dryer.

After the press section, the sheet, having a consistency ranging between about 25 wt % to 80 wt %, is transferred to a Yankee dryer 44, i.e. a pressure vessel which reduces the water content of the web. There is a dryer hood located over the Yankee dryer where heated air is projected to contribute to the sheet drying. Adhesives are sprayed to the Yankee dryer 44 to make the paper stick and to permit creping of the sheet, if any. Following the Yankee dryer 44, the sheet has a consistency of about 75 wt % to about 85 wt %. One skilled in the art will appreciate that in another process, the sheet can have a higher consistency following the Yankee dryer 44. For instance and without being limitative, the sheet can have a consistency up to about 98 wt %.

Then, a creping step can be carried out by a Yankee's doctor blade (not shown) that scrapes the paper off the cylinder surface. Simultaneously, the speed of the following elements of the paper machine are reduced to allow the creation of the crinkle (creping).

Finally, the sheet is transferred to the after dryers 46, which include a plurality of consecutive heated rolls 48 where its consistency is increased. The after dryers 46 can be a through air dryer (i.e. a honeycomb dryer) where up air goes through the sheet to finish the drying process.

As mentioned above, the antimicrobial agent and the cationizing agent are applied either at the paper machine or during the following converting step.

The application method can be selected by considering the viscosity and the concentration of the antimicrobial and cationizing agents. If these agents are diluted, an additional drying step may be required to obtain a final antimicrobial tissue paper having a consistency (or solid content) above approximately 92 wt %.

At the paper machine, the antimicrobial and cationizing agents are applied before or after the Yankee dryer 44, before the after-dryers 46. They can be applied by spraying, with applicator rolls, by a metering size press, by a rotor damping system, for instance the WEKO-RFT Rotor Damping System, by transfer rolls, for instance the systems developed by Coating & Moisturizing Systems Inc (CMS), and the like.

FIGS. 2 and 3 show two possible embodiments wherein the antimicrobial and cationizing agents are applied before the Yankee dryer 44 by spraying. In FIG. 2, the agent applicators 50*a*, 50*b* are located before either a plain press (can include a blind drilled roll), a suction press or a shoe press 52. It is appreciated that, in alternative embodiments, the process can include only one applicator, either applicator 50*a* or applicator 50*b*. The tissue paper consistency (or solid content) is about 15 wt % to 25 wt % and, in an embodiment, the tissue paper consistency is about 20 wt %.

FIG. 3 shows another embodiment of a process wherein the antimicrobial and cationizing agents are applied before the Yankee dryer 44. The features are numbered with reference numerals in the 100 series which correspond to the reference numerals of the previous embodiment.

In FIG. 3, the agent applicators 150 are located between two presses 152. The presses can be either plain presses (can include a blind drilled roll), suction presses, shoe presses or combination thereof. It is appreciated that, in alternative embodiments, the process can include several applicators. The tissue paper consistency is between about 20 wt % to 50 wt %.

If the antimicrobial and cationizing agents are applied after the Yankee dryer 44, the tissue paper consistency is above about 75 wt % and, in an embodiment, the tissue paper consistency is between about 75 wt % to about 98 wt %.

If the tissue paper is embossed (converting step), the antimicrobial agent can be applied before or after the embossing unit through applicator rolls or a spraying system (or nozzle) as shown in FIG. 4. If the antimicrobial agent is applied in the converting unit and since the addition of the antimicrobial and cationizing agents typically increases the water content of the tissue paper, further drying may be necessary. For instance and without being limitative, infra-red or air cap dryers can be used. The features are numbered with reference numerals in the 200 series which correspond to the reference numerals of the previous embodiments.

In FIG. 4*a*, the antimicrobial and cationizing agents are added by applicator rolls 260 upstream the embossing rolls 262. More particularly, the paper web 264 is unwind from a paper roll 266 and is carried between two applicator rolls 260 wherein the antimicrobial and cationizing agents are added. Then, the paper web 264 is further carried through a drying unit 268 wherein the paper web 264 is further dried. The paper web 264 is then conveyed in an embossing unit 270 including two embossing rolls 262. Finally, the paper web 264 is rolled into a roll 272.

In the alternative embodiment shown in FIG. 4*b*, the agents are added by a spray shower upstream the embossing rolls 262. In comparison with the embodiment shown in FIG. 4*a*, the antimicrobial and cationizing agents are applied by a spraying system 250. The spraying system 250 is located between the paper roll 266 and the drying unit 268.

In the alternative embodiment shown in FIG. 4*c*, the agents are added by applicator rolls 260 downstream the embossing rolls 262. More particularly, the paper web 264 is unwind from a paper roll 266 and is carried in the embossing unit 270 including two embossing rolls 262. Then, the paper web 264 is conveyed between two applicator rolls 260 wherein the antimicrobial and cationizing agents are applied. Then, the paper web 264 is further carried through a drying unit 268 wherein the paper web 264 is further dried. Finally, the dried paper web 264 is rolled into a roll 272.

In the alternative embodiment shown in FIG. 4*d*, the agents are added by a spray shower 250 downstream the embossing rolls 262. In comparison with the embodiment shown in FIG. 4*c*, the antimicrobial and cationizing agents are applied by a spraying system 250. The spraying system 250 is located between the embossing unit 270 and the drying unit 268.

In the alternative embodiment shown in FIG. 4*e*, the agents are added by applicator rolls 260. On the opposite of the above-described embodiment, the converting step does not include embossing rolls. More particularly, the paper web 264 is unwind from a paper roll 266 and is conveyed between two applicator rolls 260 wherein the antimicrobial and cationizing agents are applied. Then, the paper web 264 is further carried through a drying unit 268 wherein the paper web 264 is further dried. Finally, the dried paper web 264 is rolled into a roll 272.

In the alternative embodiment shown in FIG. 4f and in comparison with the embodiment shown in FIG. 4e, the antimicrobial and cationizing agents are applied by a spraying system 250.

The antimicrobial and cationizing agents can be also applied by creating a drop pattern (e.g. inkjet) or by printing (e.g. rotogravure or flexography).

If the antimicrobial and cationizing agents are applied during the converting step, the tissue paper consistency is above approximately 90 wt %. As mentioned above, an additional drying step may be necessary to increase the consistency above about 92 wt %.

At the end of the paper machine, the antimicrobial paper is winded into parent rolls for further processing in the converting steps such as embossing, rewinding, and cutting into small roll products for paper dispensers or folded products.

Since a portion of the antimicrobial agent is released from the tissue paper when wetted, it is not necessary to fully cover the tissue paper surfaces with the antimicrobial agent and the cationizing agent. For instance, the antimicrobial agent and/or the cationizing agent can be applied either on only one face of the tissue paper or on both faces.

The antimicrobial tissue paper may come in white, as well as an array of colors, for instance and without being limitative, it can be pastel blue or green by adding dyes or pigments.

The antimicrobial tissue paper can be used for hygiene purposes such as hand towels, facial tissues (paper handkerchiefs), napkins, bathroom (toilet) tissues, wipes, and household towels.

The cationic antimicrobial agent interacts with the anionic paper fibres through electrostatic interactions. In addition, the hydrophobic part of the antimicrobial agent can interact with hydrophobic domain of fibres. For paper treated with a cationizing agent such as a cationic polymer, the release of the antimicrobial agent is improved.

The amount of antimicrobial agent released will be highly dependent on the method used to retrieve it from the paper. A lab blender method is used to extract the benzalkonium chloride. Following the extraction, the concentration of the benzalkonium chloride present in water is measured by a method such as and without being limitative biphasic titration or high performance liquid chromatography (HPLC). Concentrations of the benzalkonium chloride released from the paper are expressed on a weight by weight basis. One skilled in the art will appreciate that other methods can be developed for other antimicrobial agents.

Typically, the amount of benzalkonium chloride released with the lab blender method is higher than when wiping hands or a surface with the antimicrobial tissue paper.

The first step of this method consists in extracting the benzalkonium chloride present in the paper hand towel (for instance, 8×12 inches) or any other tissue paper as follow: the sheet previously weighed (±0.01 g) is folded in four and placed in a 500 mL mini blender cup. Then, 50 mL of deionized water are added. The sheet is disintegrated for about 10 seconds. The resulting paper pulp is left five (5) minutes to settle down. The paper pulp is filtered and the concentration of benzalkonium chloride is measured in the filtrate by a method such as and without being limitative biphasic titration or HPLC.

Example A

The following tests show the antimicrobial agent release rate as a function of its concentration in the paper substrate.

The first two sets of paper substrates were prepared with different concentrations of antimicrobial agent, and more particularly benzalkonium chloride. The first paper substrate set was prepared with virgin fibres while the second paper substrate set was prepared with recycled fibres. The cationizing agent was a polyepichlorohydrin-dimethylamine (Epi-DMA) of substantially low molecular weight (about 20 to 50 kDa) and high charge density (between about 6 and 9.9 Equiv/Kg dry) which concentration was about 1.5 wt %.

Two other sets of paper substrates were prepared with different concentrations of antimicrobial agent but were substantially free of cationizing agent.

Figure 5:
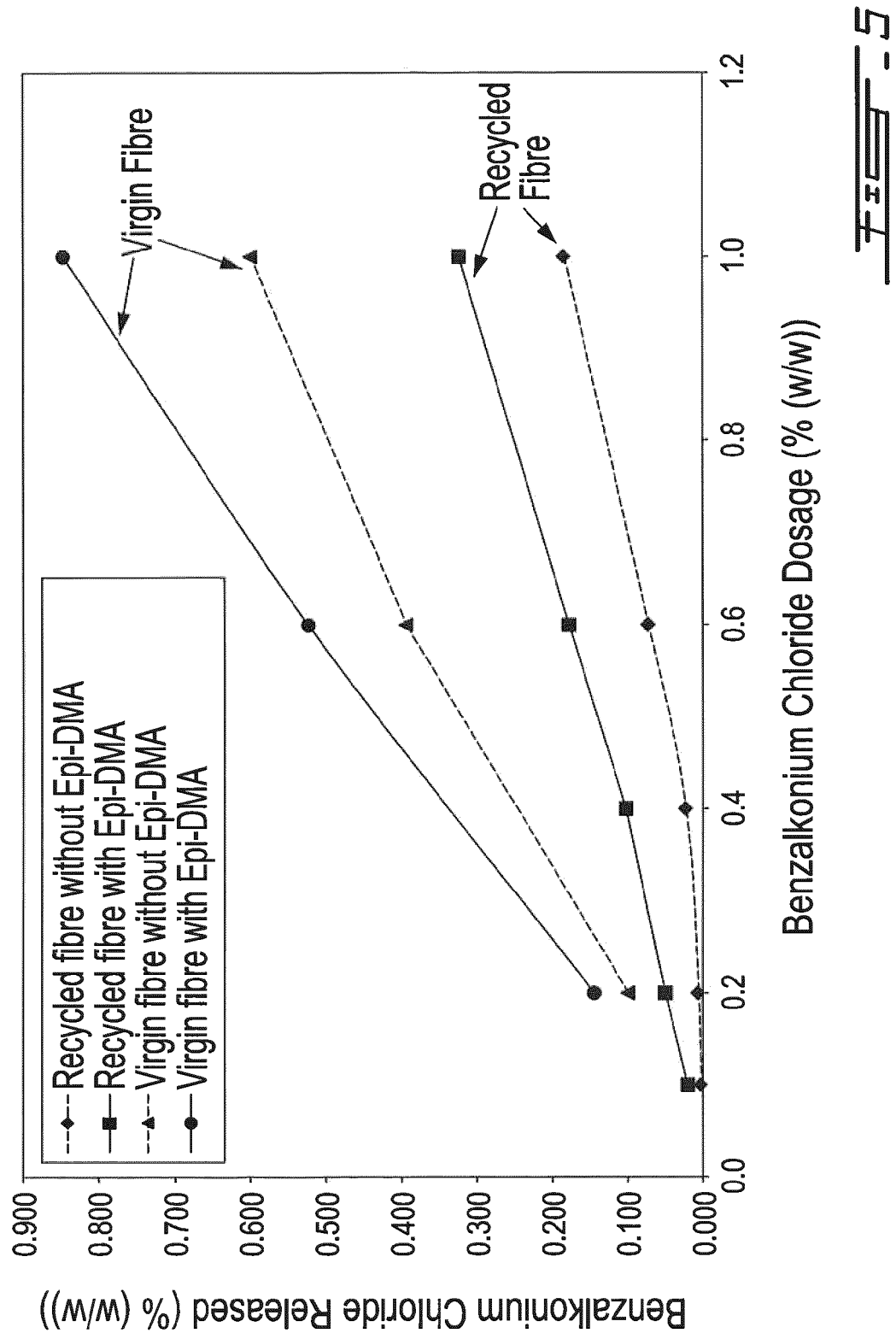
FIG. 5 is a graph showing the antimicrobial agent release rate as a function of its concentration in a paper substrate wherein the cationizing agent is polyepichlorohydrin-dimethylamine (EPI-DMA)

FIG. 5 shows the antimicrobial agent release rate for all sets of papers. It is shown that, for the antimicrobial papers which are substantially free of cationizing agent, a certain proportion of the antimicrobial agent is released but, when combined with the cationizing agent, for the same concentration of antimicrobial agent, the antimicrobial agent release rate is significantly higher.

Furthermore, higher antimicrobial agent release is obtained for paper substrates made with virgin fibres in comparison with paper substrates made of recycled fibres. This is due to the higher anionic charge content of the recycled fibres. The benzalkonium chloride being cationic, a certain proportion of BC might be used to neutralize the paper anionic charges.

Two other sets of paper substrates were prepared with different concentrations of antimicrobial agent, and more particularly benzalkonium chloride. For both sets, the paper substrate was prepared with recycled fibres. The cationizing agent was a polyamidoamine-epichlorohydrin (PAAE) of substantially low molecular weight (between about 40 and 200 kDa) and medium charge density (between about 2 and 4 Equiv/Kg dry). The first set of paper substrates included about 1.2 wt % of cationizing agent while the second set of paper substrates was substantially free of cationizing agent.

Figure 6:
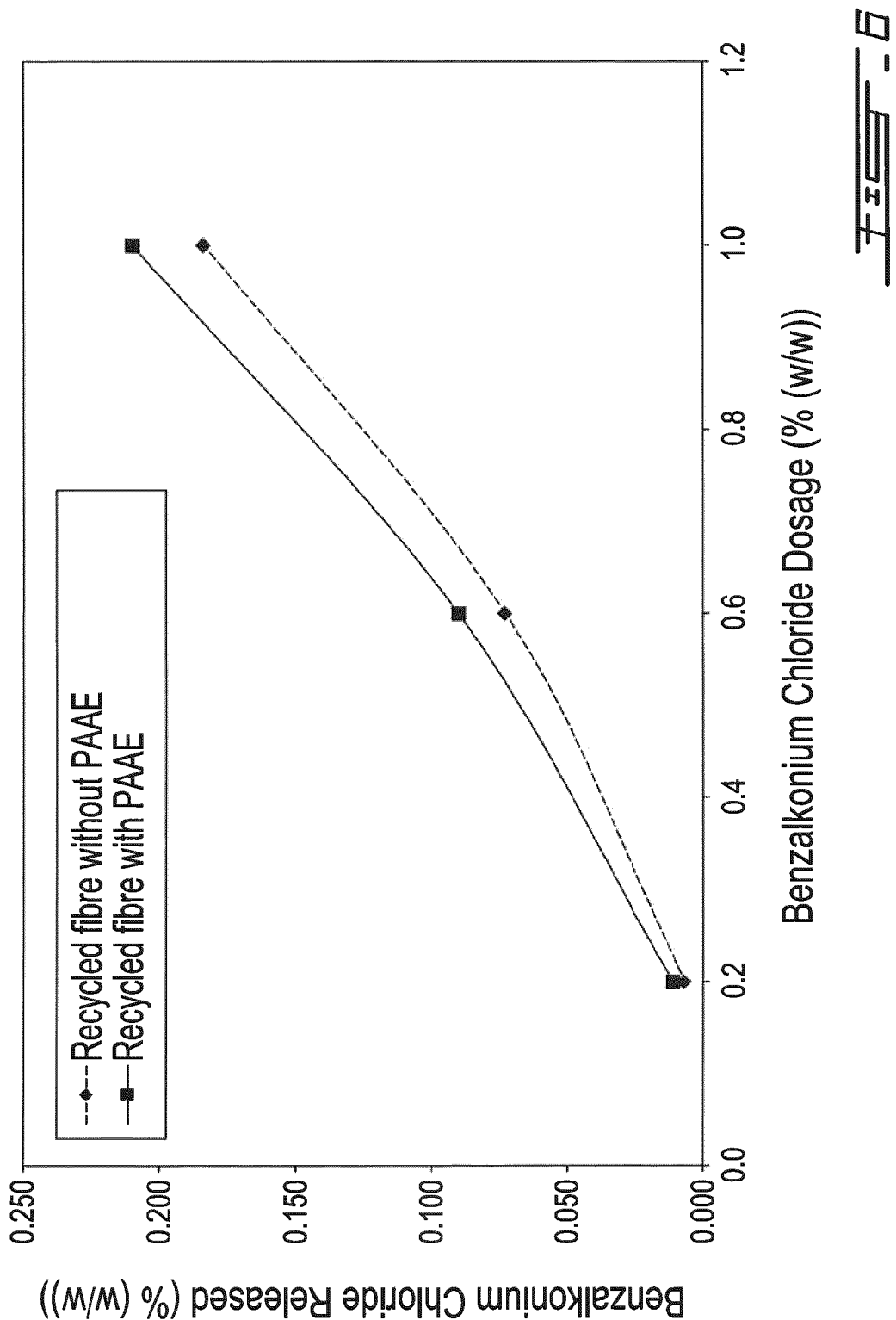
FIG. 6 is a graph showing the antimicrobial agent release rate as a function of its concentration in a paper substrate wherein the cationizing agent is a polyamidoamine-epichlorohydrin (PAAE)

FIG. 6 shows the antimicrobial agent release rate for all papers. Once again, it is shown that, for the antimicrobial papers which are substantially free of cationizing agent, a certain proportion of the antimicrobial agent can be released but, when combined with the cationizing agent, for the same concentration of antimicrobial agent, the antimicrobial agent release rate is higher.

Example B

The following tests show the antimicrobial agent release rate as a function of the molecular weight of the cationizing agent. The concentration of the cationizing agent was about 1.2 wt %. The antimicrobial agent was benzalkonium chloride with a dosage of about 1 wt %.

Figure 7:
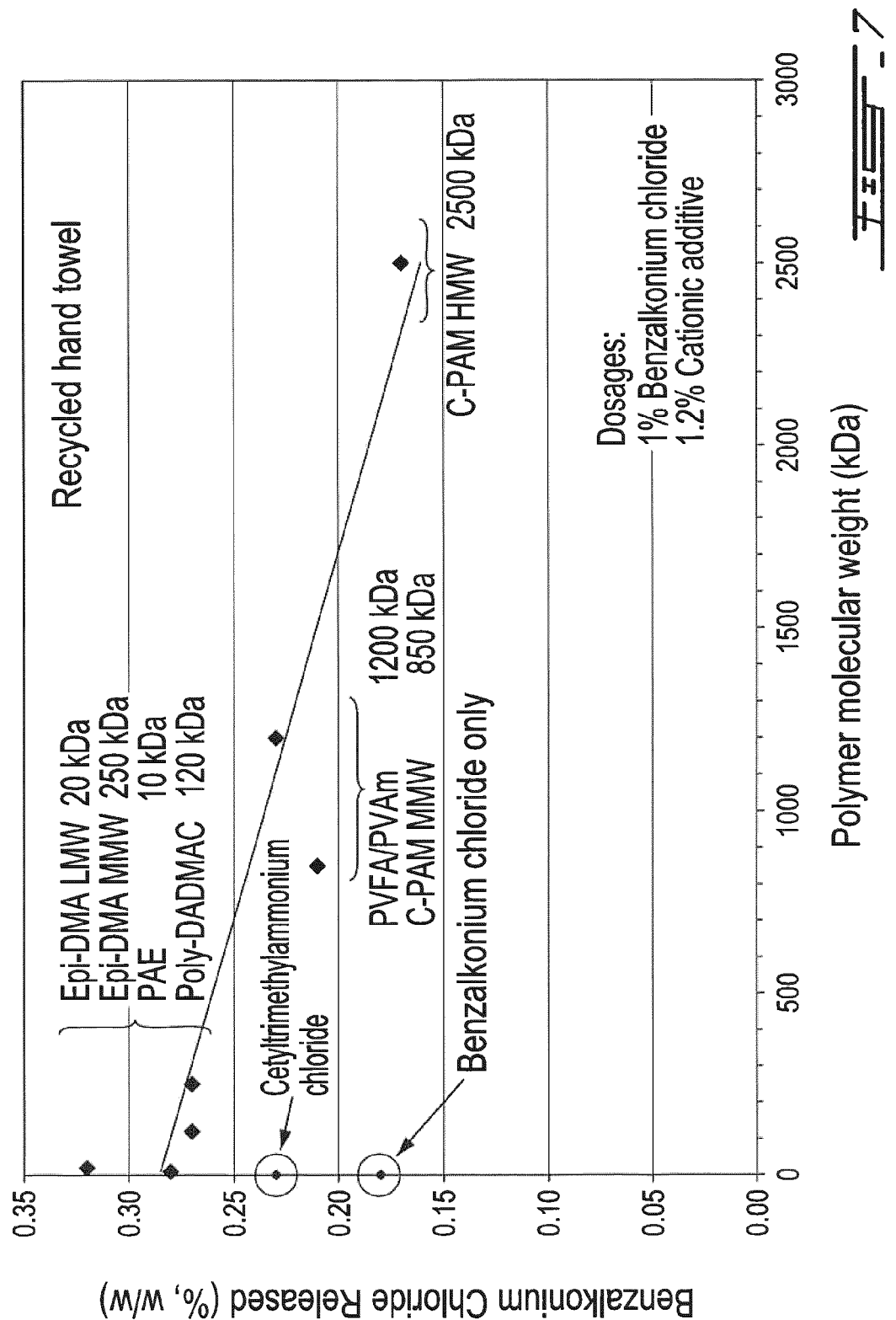
FIG. 7 is a graph showing the antimicrobial agent release rate as a function of the molecular weight of several cationizing agents.

FIG. 7 and Table 3 show the benzalkonium chloride release rate as a function of the molecular weight of several cationizing agents. The following cationizing agents were tested: polyepichlorohydrin-dimethylamine (Epi-DMA) of relatively low molecular weight (about 20 kDa), polyepichlorohydrin-dimethylamine (Epi-DMA) of relatively medium molecular weight (about 250 kDa), polyamine-epichlorohydrin (PAE) (about 10 kDa), polydiallyldimethylammonium chloride (poly-DADMAC) (about 120 kDa), cetyltrimethylammonium (about 0.32 kDa), partially hydrolyzed polyvinyl formamide (PVFA/PVAm) (about 1200 kDa), cationic polyacrylamide (C-PAM) of relatively medium molecular weight (about 850 kDa), and C-PAM of relatively high molecular weight (about 2 500 kDa). One paper substrate also included solely the antimicrobial agent, i.e. the paper was substantially free of cationizing agent.

TABLE 3

Benzalkonium chloride release rate for several cationizing agents.

| Cationic Agent | Charge Density (eq/kg) | Benzalkonium chloride released (% (w/w)) | Measured MW (kDa) | Charge ratio[a] |
|---|---|---|---|---|
| EPI-DMA (low molecular weight) | 7.94 | 0.32 | 21.3 | 1.83 |
| EPI-DMA | 8.02 | 0.30 | 150[b] | 1.84 |
| Epi-DMA (medium molecular weight) | 7.54 | 0.27 | 250.9 | 1.76 |
| Poly-DADMAC | 6.94 | 0.27 | 122.0 | 1.65 |
| PEI | 4.43 | 0.25 | n.a | 1.21 |
| PAAE | 1.25 | 0.21 | n.a | 0.65 |
| PAE | 7.53 | 0.28 | 7.2 | 1.76 |
| C-PAM (medium molecular weight) | 3.70 | 0.21 | 866.8 | 1.08 |
| PVFA/PVAm | 5.00 | 0.23 | 1193.3 | 1.31 |
| C-PAM (high molecular weight) | 1.20 | 0.17 | 2537.3 | 0.64 |
| Cationic starch | 0.62 | 0.16 | n.a | 0.54 |
| G-PAM | 0.39 | 0.16 | n.a | 0.50 |
| Cetyltrimethyl-ammonium chloride | 3.76 | 0.23 | 0.32 | 1.09 |
| PAMAM dendrimer generation 5 | 3.52 | 0.18 | n.a | 1.05 |
| Without cationizing agent | — | 0.18 | n.a | 0.43 |

[a]Charge ratio: Cationic charges from additives over anionic charges from fibres.
[b]MW supplied by the manufacturer.

One skilled in the art will appreciate that the performance of the cationizing agent varies in accordance with its concentration. For instance, lower concentration of cationizing agents having a higher charge density are required to promote release of the antimicrobial agent while higher concentration of cationizing agents having a lower charge density are required to neutralize the paper anionic charges and promote release of the antimicrobial agent.

Figure 8:
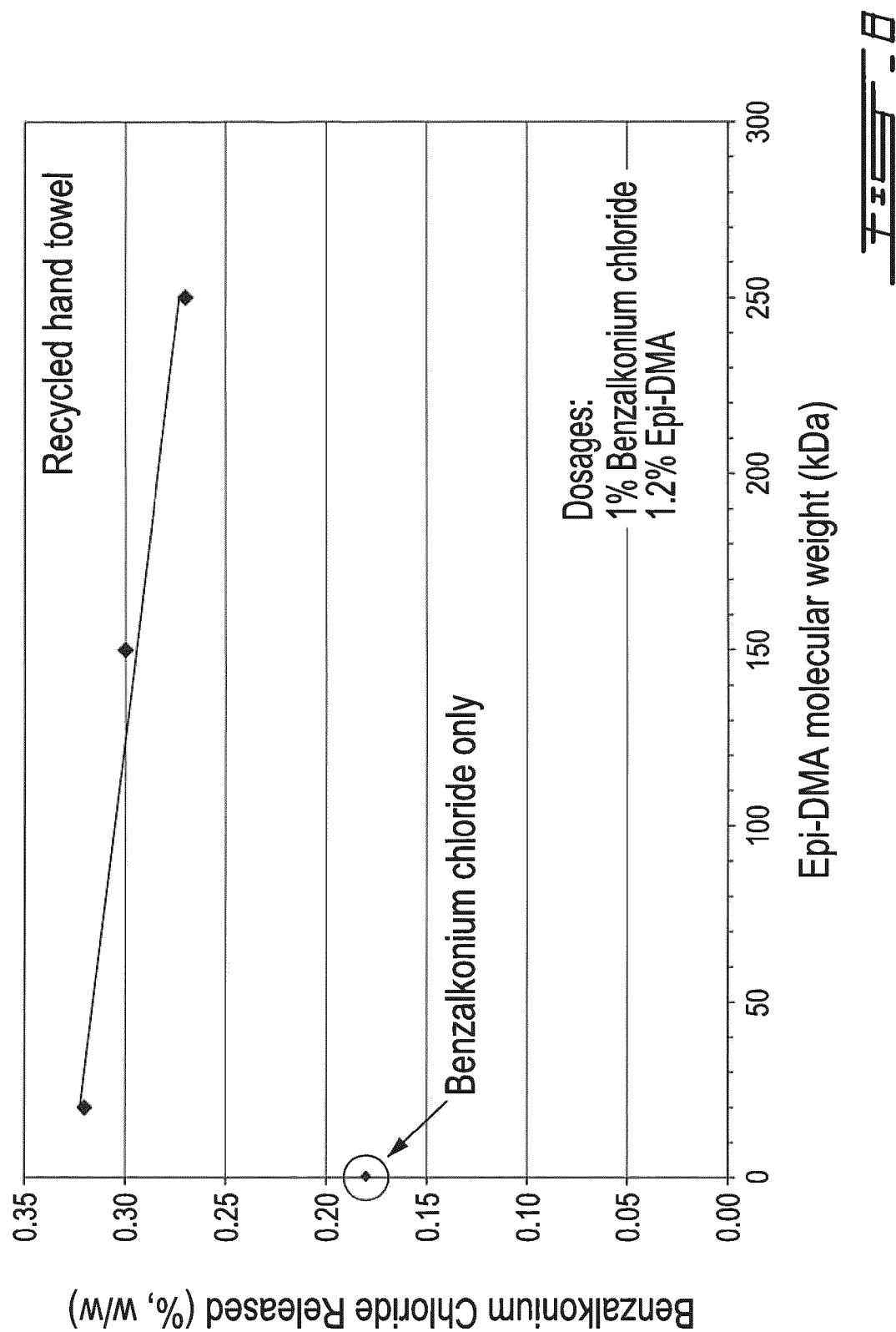
FIG. 8 is a graph showing the antimicrobial agent release rate as a function of three polyepichlorohydrin-dimethylamine (EPI-DMA) cationizing agents of different molecular weights (20 kDa, 150 kDa, and 250 kDa)

FIG. 8 also shows the antimicrobial agent release rate as a function of the molecular weight of one cationizing agent. More particularly, three polyepichlorohydrin-dimethylamine cationizing agents of different molecular weights were tested: 20 kDa, 150 kDa, and 250 kDa.

For all cationizing agents, the paper substrate was a hand towel made of recycled pulp.

Cationizing agents having lower molecular weight enhances antimicrobial agent release. Highest antimicrobial agent release was obtained for cationizing agents having a molecular weight substantially equal or lower than 250 kDa.

Cationizing polymers with a relatively high charge density (about greater than 5 eq/kg) and low molecular weight (about lower than 250 kDa, e.g. coagulants) have shown good efficiency to cationize the cellulosic fibres, thus inducing a higher level of antimicrobial agent released. For relatively low molecular weight polymers, both bulk and surface charges of cellulosic fibres seem neutralized. However, the release of the antimicrobial agent is mostly related to the bulk charges, which represent more than 90% of total charges. Higher molecular weight cationizing polymers will tend to remain on fibre surface (with limited diffusion) and thus reacting mainly with surface charges. Cationizing polymers having medium charge densities (about between 2 eq/kg and 5 eq/kg) and medium molecular weight (about between 250 kDa and 1000 kDa) have a lower cationization capacity and intermediate capacity to induce the release of the antimicrobial agent. Lower charge density cationizing polymers (lower than 2 eq/kg, e.g. starch, G-PAM) have lower capacity to cationize the fibres, i.e. total anionic charges, and showed limited capacity to induce the antimicrobial agent release.

The above interpretations are based on constant dosage of cationizing polymer (12 kg/T).

A person skilled in the art will appreciate that an increase of cationizing polymer dosage could compensate for the lack of charge density of some cationization polymers to induce higher antimicrobial agent released.

Example C

Tables 4 and 5 show the charge ratio in the production of the antimicrobial paper. The charge ratio is calculated as the cationic charges from the cationizing agent and the antimicrobial agent over the anionic charges from fibres. For all examples, the antimicrobial agent was benzalkonium chloride and the cationizing agent was polyepichlorohydrin-dimethylamine. Table 4 shows the charge ratio for a recycled pulp hand towel; and Table 5 shows the charge ratio for a virgin bleached Kraft hand towel.

TABLE 4

Recycled deinked pulp (DIP) hand towel

| | Charge density (equiv/kg) | Dosage (kg/T) | Total charge (equiv/T of fibres) | Charge ratio | Antimicrobial agent release (wt %) |
|---|---|---|---|---|---|
| Fibres | −0.068 | N/A | −68 | 1.8 cationic over anionic charges | 0.32 |
| Cationizing agent | +7.94 | 12 | +95 | | |
| Antimicrobial agent | +2.9 | 10 | +29 | | |

N/A: not applicable

TABLE 5

Virgin bleached Kraft hand towel

| | Charge density (equiv/kg) | Dosage (kg/T) | Total charge (equiv/T of fibres) | Charge ratio | Antimicrobial agent release (wt %) |
|---|---|---|---|---|---|
| Fibres | −0.033 | N/A | −33 | 4.5 cationic over anionic charges | 0.85 |
| Cationizing agent | +7.94 | 15 | +119 | | |
| Antimicrobial agent | +2.9 | 10 | +29 | | |

N/A: not applicable

Figure 9:
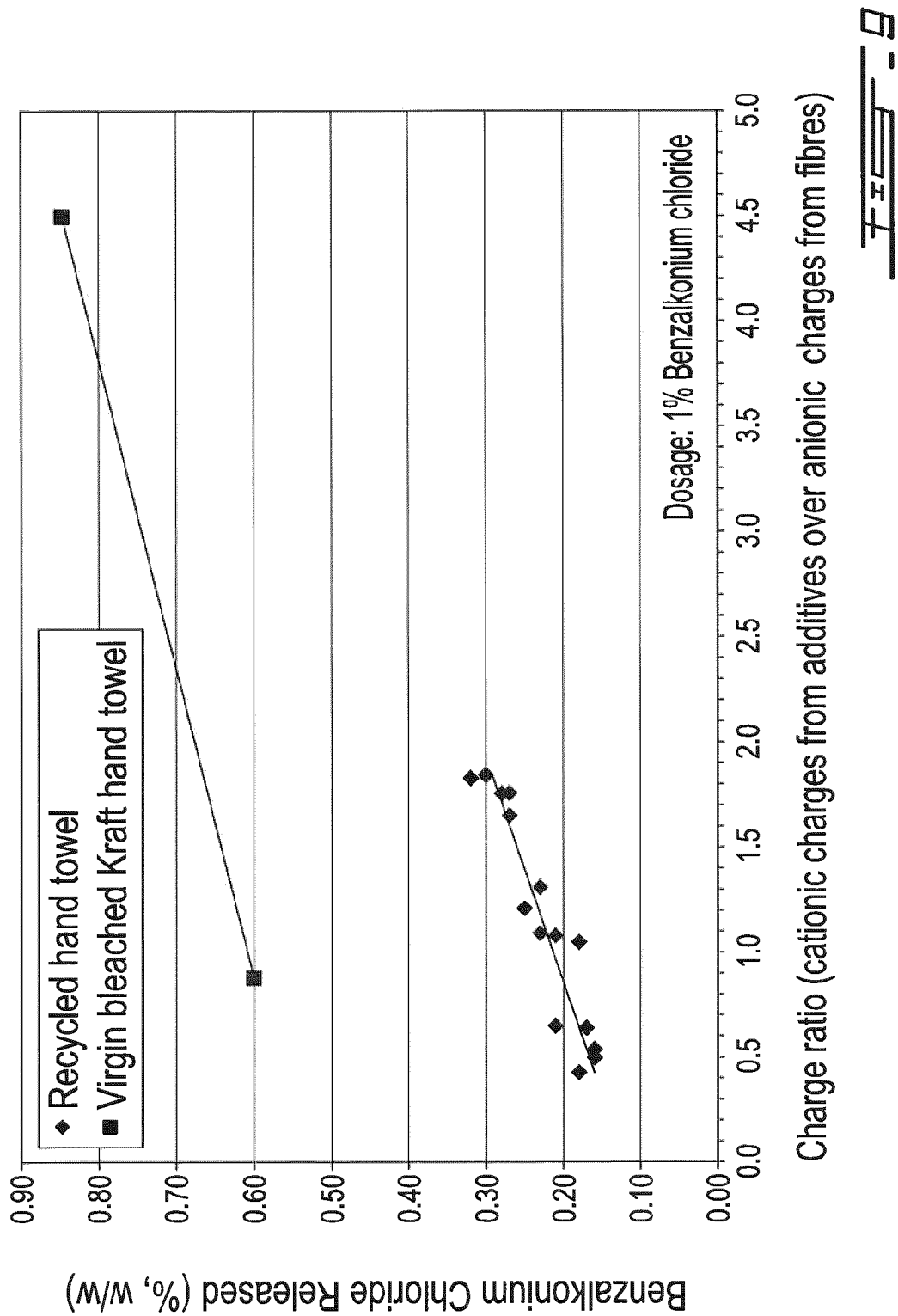
FIG. 9 is a graph showing the antimicrobial agent release as a function of the charge ratio for recycled and virgin bleached Kraft hand towels.

FIG. 9 shows the antimicrobial agent release as a function of the charge ratio for recycled and virgin bleached Kraft hand towels. Papers having higher charge ratio have a higher antimicrobial agent release when wetted.

Example D

Ten sheets of embossed white tissue paper having a grammage of 25 lbs/3000 ft² (about 40 grams per square meter) were tested with several bacteria. The antimicrobial tissue paper was prepared in an industrial continuous manufacturing process wherein a solution including BC as antimicrobial agent and polyepichlorohydrin-dimethylamine as cationizing agent was sprayed on the paper web. Their concentration on the resulting paper was respectively about 0.3 wt % and 1.3 wt %.

The antimicrobial efficiency of the tissue papers and, more particularly, paper towels, was tested with several bacteria and, in particular, with *Staphylococcus aureus* ATCC 6538, *Staphylococcus aureus* ATCC 25929, *Listeria monocytogenes* Scott 3, *Streptococcus agalactiae*, *Streptococcus* M3, and *Enterococcus faecium*. An agar diffusion assay (ADA) of Berridge and Barret (1952) was used as a reference method for the detection of the antimicrobial activity of the tissue paper samples. In summary, tryptic soy medium containing 0.75% (w/v) agar and 1% (w/v) Tween 20 was autoclaved and cooled to 45° C. in a temperature-controlled water bath. An overnight culture of one of the target bacteria was then added at a final concentration of 1% (v/v) and 30 ml of this suspension was poured into each sterile Petri plate (100×15 mm). Following solidification, a piece (2.5 cm×2.5 cm) of tissue paper samples including antimicrobial tissue papers and a control tissue paper, i.e. a paper substantially free of antimicrobial and cationizing agents, moisturized with 4 drops of sterile water was deposited on the surface of agar media plates. The plates were then incubated at 30° C. or 37° C., depending on the target bacterial strain, for at least 24 h to give a well-defined inhibition zone. Inhibition zone diameters were measured to the nearest 0.1 mm using a calliper. For oval inhibition zones, the mean of the largest and shortest diameters was calculated as shown in Table 6.

Results showed that relatively important inhibition zones are obtained with antimicrobial papers in comparison with the control paper. The diameters of the inhibition zone vary in function of the bacteria. Furthermore, higher antimicrobial agent release rates are associated with large inhibition zones for the same bacteria.

TABLE 6

Bacterial inhibition zones for two tissue papers having BC release rates of 0.07 wt % and 0.09 wt %.

| Bacteria tested | Inhibition zones in millimeter (mm) | | |
| --- | --- | --- | --- |
| | 0% of BC released | 0.07% of BC released | 0.09% of BC released |
| *Staphylococcus aureus* ATCC 6538 | 0.0 | 28.5 | 29.5 |
| *Staphylococcus aureus* ATCC 25929 | 0.0 | 26.3 | 28.0 |
| *Listeria monocytogenes* Scott 3 | 0.0 | 26.8 | 27.8 |
| *Streptococcus agalactiae* | 0.0 | 26.0 | 27.8 |
| *Streptococcus* M3 | 0.0 | 25.8 | 26.8 |
| *Enterococcus faecium* | 0.0 | 26.0 | 26.8 |

Once again, one skilled in the art will appreciate that the antimicrobial paper performances vary in accordance with the bacteria present as well as the antimicrobial agent(s) contained in the antimicrobial paper.

Use of the cationizing polymer can either increase the antimicrobial agent release or reduce the antimicrobial agent concentration added to the paper substrate for the same antimicrobial agent release.

As mentioned above, it is appreciated that the total anionic charges of the tissue paper can vary. Thus, the cationizing agent concentration in the tissue paper can be varied accordingly.

Furthermore, it was observed that unbleached virgin or unbleached recycled tissue papers have higher total anionic charges than white tissue paper. Therefore, higher levels of cationizing agent may be necessary to at least partially neutralize the paper anionic charges for unbleached virgin or recycled tissue papers.

It is appreciated that the antimicrobial tissue paper can be used to make a large range of products with different attributes and quality requirement demands and with variable properties such as, without being limitative, strength, absorbency, basis weight (or grammage), thickness, brightness, stretch, appearance, and the like.

Furthermore, the antimicrobial paper is substantially emollient free and the antimicrobial agent is transferred from the paper web to the surface through an aqueous solution such as water.

Several alternative embodiments and examples have been described and illustrated herein. The embodiments of the invention described above are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention. The scope of the invention is therefore intended to be limited solely by the scope of the appended claims.

The invention claimed is:

1. A dry antimicrobial wiping paper comprising a paper web having a grammage between 10 and 60 grams per square meter, a cationizing agent in a concentration ranging between 0.05 wt % and 5 wt % and sufficient to at least one of partially neutralize, neutralize and cationize the paper web having a paper web consistency above about 15 wt %, a water-soluble antimicrobial agent in a concentration ranging between 0.01 wt % and 3 wt %, wherein a portion of the antimicrobial agent is released when the antimicrobial wiping paper is wetted by wiping a wet surface.

2. The dry antimicrobial wiping paper as claimed in claim 1, wherein the antimicrobial wiping paper has an antimicrobial agent release of above about 0.01 wt % when wetted by wiping the wet surface.

3. The dry antimicrobial wiping paper as claimed in claim 1, wherein the antimicrobial agent release is between about 0.05 wt % and about 3 wt % when wetted by wiping the wet surface.

4. The dry antimicrobial wiping paper as claimed in claim 1, wherein the antimicrobial agent comprises a cationic surfactant and the antimicrobial wiping paper has a cationic charge.

5. The dry antimicrobial wiping paper as claimed in claim 1, wherein the antimicrobial agent comprises at least one amine salt.

6. The dry antimicrobial wiping paper as claimed in claim 1, wherein the antimicrobial agent comprises at least one quaternary ammonium.

7. The dry antimicrobial wiping paper as claimed in claim 1, wherein the cationizing agent is in a concentration below 2.5 wt %, has a charge density above about 2 eq/kg and has a molecular weight below 1000 kDa.

8. The dry antimicrobial wiping paper as claimed in claim 7, wherein the canonizing agent has a charge density above about 5 eq/kg.

9. The dry antimicrobial wiping paper as claimed in claim 1, wherein the cationizing agent comprises an organic coagulant.

10. The dry antimicrobial wiping paper as claimed in claim 1, wherein the cationizing agent is at least one of a polyamine, a polyDADMAC, a PEI, a PAE, a PAAE, and a PVAm.

11. The dry antimicrobial wiping paper as claimed in claim 1, wherein the paper web has a thickness ranging between 125 and 1000 micrometers.

12. The dry antimicrobial wiping paper as claimed in claim 1, wherein the paper web comprises one to five superposed paper plies.

13. The dry antimicrobial wiping paper as claimed in claim 1, wherein the paper web consistency is between 75 wt % and 98 wt % when the cationizing agent and the antimicrobial agent are added to the paper web.

14. The dry antimicrobial wiping paper as claimed in claim 1, wherein the paper web consistency is between 20 wt % and 50 wt % when the cationizing agent and the antimicrobial agent are added to the paper web.

15. A process for manufacturing a dry antimicrobial wiping paper as claimed in claim 1, comprising:
    obtaining the paper web;
    applying the cationizing agent and the water-soluble antimicrobial agent to the paper web; and
    drying the paper web including the cationizing agent and the microbial agent to increase the paper web consistency above 92 wt %,
    wherein a portion of the antimicrobial agent is released when the antimicrobial wiping paper is wetted by wiping a wet surface.

16. A process as claimed in claim 15, wherein the antimicrobial wiping paper has an antimicrobial agent release of above about 0.01 wt % when wetted by wiping the wet surface.

17. A process as claimed in claim 15, wherein the antimicrobial agent is a cationic surfactant and the antimicrobial wiping paper has a cationic charge.

18. A process as claimed in claim 15, wherein the cationizing agent is in a concentration below 2.5 wt %, has a charge density above about 2 eq/kg, and has a molecular weight below 1000 kDa.

19. A process as claimed in claim 15, wherein the paper web has a thickness ranging between 125 and 1000 micrometers.

20. A process as claimed claim 15, wherein the cationizing agent and the antimicrobial agent are applied to the paper web on a paper machine at an end of a forming section or following a Yankee dryer and before at least one afterdryer.

21. A process as claimed in claim 15, wherein said applying further comprises spraying the cationizing agent and the antimicrobial agent to the paper web.

22. A process as claimed in claim 15, further comprising applying the cationizing agent and the antimicrobial agent to the paper web when the paper web consistency is between 75 wt % and 98 wt %.

23. A process as claimed in claim 15, further comprising applying the cationizing agent and the antimicrobial agent to the paper web when the paper web consistency is between 20 wt % and 50 wt %.

24. A dry antimicrobial wiping paper comprising a paper web including a cationizing agent in a concentration ranging between 0.05 wt % and 5 wt % and sufficient to at least one of partially neutralize, neutralize and cationize the paper web, a water soluble antimicrobial agent in a concentration ranging between 0.01 wt % and 3 wt % and having an antimicrobial agent release rate of above about 0.01 wt % when wetted by wiping a wet surface.

25. The dry antimicrobial wiping paper as claimed in claim 24, the antimicrobial agent and the cationizing agent being added to the paper web having a paper web consistency above 15 wt %.

26. The dry antimicrobial wiping paper as claimed in claim 24, wherein the paper web has a grammage between 10 and 60 grams per square meter.

27. The dry antimicrobial wiping paper as claimed in claim 24, wherein the antimicrobial wiping paper has an antimicrobial agent release of above about 0.05 wt % when wetted by wiping the wet surface.

28. The dry antimicrobial wiping paper as claimed in claim 24, wherein the antimicrobial agent is a cationic surfactant and the antimicrobial wiping paper has a cationic charge.

29. The dry antimicrobial wiping paper as claimed in claim 24, wherein the cationizing agent is in a concentration below 2.5 wt %, has a charge density above about 2 eq/kg, and has a molecular weight below 1000 kDa.

30. The dry antimicrobial wiping paper as claimed in claim 24, wherein the cationizing agent is at least one of a polyamine, a polyDADMAC, a PEI, a PAE, a PAAE, and a PVAm.

31. The dry antimicrobial wiping paper as claimed in claim 24, wherein the paper web has a thickness ranging between 125 and 1000 micrometers.

32. The dry antimicrobial wiping paper as claimed in claim 1, wherein the paper web consistency is above 15 wt % when the antimicrobial agent and the cationizing agent are added to the paper web.

33. A process as claimed in claim 15, wherein the paper web consistency is above 15 wt % when applying the cationizing agent and the antimicrobial agent.

* * * * *